United States Patent [19]

Husbands

[11] 4,089,885

[45] May 16, 1978

[54] PROSTAGLANDIN DERIVATIVES

[75] Inventor: George E. M. Husbands, Devon, Pa.

[73] Assignee: American Home Products Corporation, New York, N.Y.

[21] Appl. No.: 739,364

[22] Filed: Nov. 5, 1976

[51] Int. Cl.$^2$ .................. C07C 177/00; C07F 7/18
[52] U.S. Cl. .................. 260/448.8 R; 260/514 D; 424/305; 424/317; 560/121
[58] Field of Search ..... 260/468 D, 448 CA, 448.8 R

[56] References Cited

U.S. PATENT DOCUMENTS 3,996,255  12/1976  Strike et al. .................. 260/448.8 R

*Primary Examiner*—Robert Gersil
*Attorney, Agent, or Firm*—Robert Wiser

[57] ABSTRACT

Derivatives of 13,14-dihydro-PGE$_2$ and 5,6; 13,14-tetrahydro-PGE$_2$ are prepared. These new compounds not heretofore found in nature display activity as bronchodilator agents.

4 Claims, 1 Drawing Figure

PROSTAGLANDIN DERIVATIVES

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation and the ability to reduce gastric secretion.

The present invention concerns $PGE_2$ derivatives in which the 13,14-double bond (using the prostanoic acid numbering system) has been reduced. The invention also concerns certain $PGE_2$ derivatives in which the 5,6-double bond has additionally been reduced. Further, there is an ethynyl group at the 15-position in addition to the normally present hydroxyl group. The preparation of, for example, the tris-(trimethylsilyl) derivatives of $PGF_2$ and tetrahydro-$PGF_2$, from which the compounds of the instant invention may readily be prepared is described in U.S. Pat. No. 3,804,889.

United States patent application Ser. No. 568,212 now U.S. Pat. No. 4,001,314 discloses, among others, 15-ethynyl-$PGE_2$ and 15-ethynyl-$PGE_1$. Belgian Pat. No. 805,111 discloses, among others, 13,14-dihydro,15-alkyl-$PGE_2$. Biochemical Medicine, 11, 298 (1974) discloses 15-keto-13,14-dihydro-$PGF_{2\alpha}$.

SUMMARY OF THE INVENTION

The invention sought to be patented in its first composition aspect resides in the concept of a chemical compound of the structure:

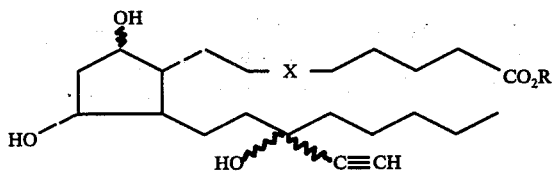

wherein X is a single bond or a cis double bond, and R is hydrogen, alkyl of from 1 to 6 carbon atoms, an alkali metal cation, or a pharmacologically acceptable cation derived from ammonia or a basic amine.

The tangible embodiments of the first composition aspect of the invention possess the inherent general physical properties of being clear to yellow oils, or crystalline solids and when R is hydrogen, are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of being intermediates for the synthesis of the embodiments of the third composition aspect of the invention. In addition, when X is a cis double bond and the 9 hydroxyl substituent is in the β sterochemical configuration, the compositions exert bronchodilating effects in warm-blooded animals, which effects are evidenced by pharmacological evaluation according to standard test procedures.

The invention sought to be patented in a first subgeneric aspect of the first composition aspect resides in the concept of a chemical compound of the structure:

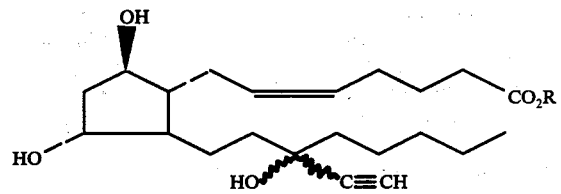

wherein R is as defined above.

The invention sought to be patented in a second subgeneric aspect of the first composition aspect resides in the concept of a chemical compound of the structure:

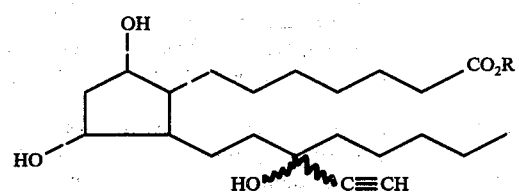

wherein R is as defined above.

The invention sought to be patented in its second composition aspect resides in the concept of a chemical compound of the structure:

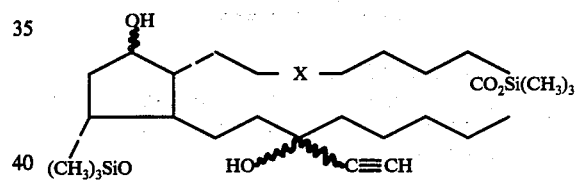

wherein X is a single bond or a cis double bond.

The tangible embodiments of the second composition aspect of the invention possess the inherent general physical properties of being clear to yellow oils, which are generally soluble in organic solvents such as methanol, ethyl acetate, and ether. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of being intermediates for the synthesis of the embodiments of the third composition aspect of the invention.

The invention sought to be patented in its third composition aspect resides in the concept of a chemical compound of the structure:

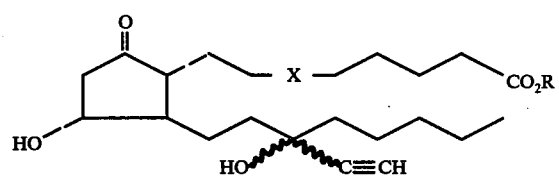

wherein X is a single bond or a cis double bond and R is hydrogen, alkyl of from 1 to 6 carbon atoms, an alkali metal cation, or a pharmacologically acceptable cation derived from ammonia or a basic amine.

The tangible embodiments of the third composition aspect of the invention possess the inherent general physical properties of being clear to yellow oils, or crystalline solids and when R is hydrogen, are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention possess the inherent applied use characteristic of exerting bronchodilating effects in warm-blooded animals, which effects are evidenced by pharmacological evaluation according to standard procedures.

The invention sought to be patented in a first subgeneric aspect of the third composition aspect resides in the concept of a chemical compound of the structure:

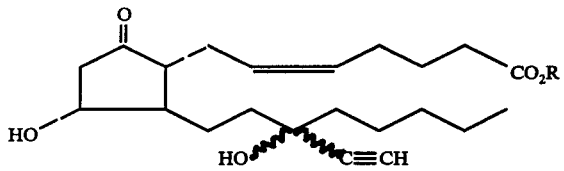

wherein R is as defined above.

The invention sought to be patented in a second subgeneric aspect of the third composition aspect resides in the concept of a chemical compound of the structure:

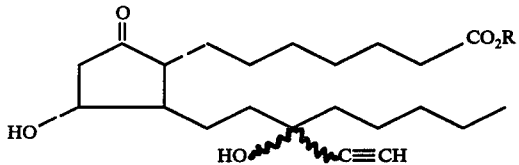

wherein R is as defined above.

The invention sought to be patented in a third subgeneric aspect of the third composition aspect resides in the concept of a chemical compound of the structure:

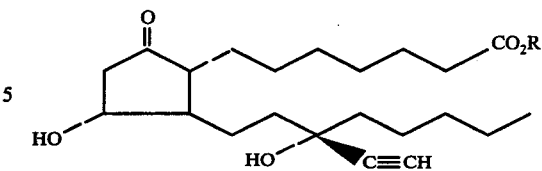

wherein R is as defined above.

The invention sought to be patented in its fourth composition aspect resides in the concept of a chemical compound of the structure:

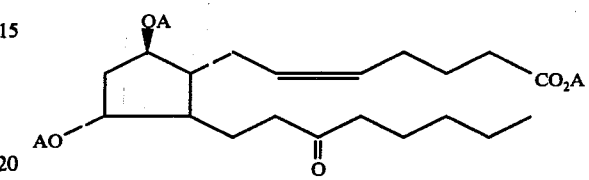

wherein A is hydrogen or $Si(CH_3)_3$.

The tangible embodiments of the fourth composition aspect of the invention possess the inherent general physical properties of being clear to yellow oils, and are generally soluble in organic solvents such as methanol, ethyl acetate, and ether. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristics of being intermediates for the synthesis of the embodiments of the third composition aspect of the invention.

The invention sought to be patented in a first specific aspect of the fourth composition aspect resides in the concept of a chemical compound of the structure:

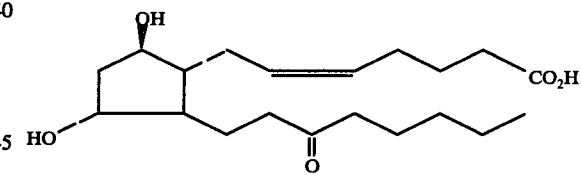

The invention sought to be patented in a second specific aspect of the fourth composition aspect aspect resides in the concept of a chemical compound of the structure:

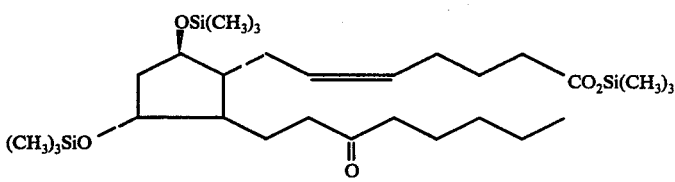

DESCRIPTION OF THE PREFERRED EMBODIMENTS

Figure 1:
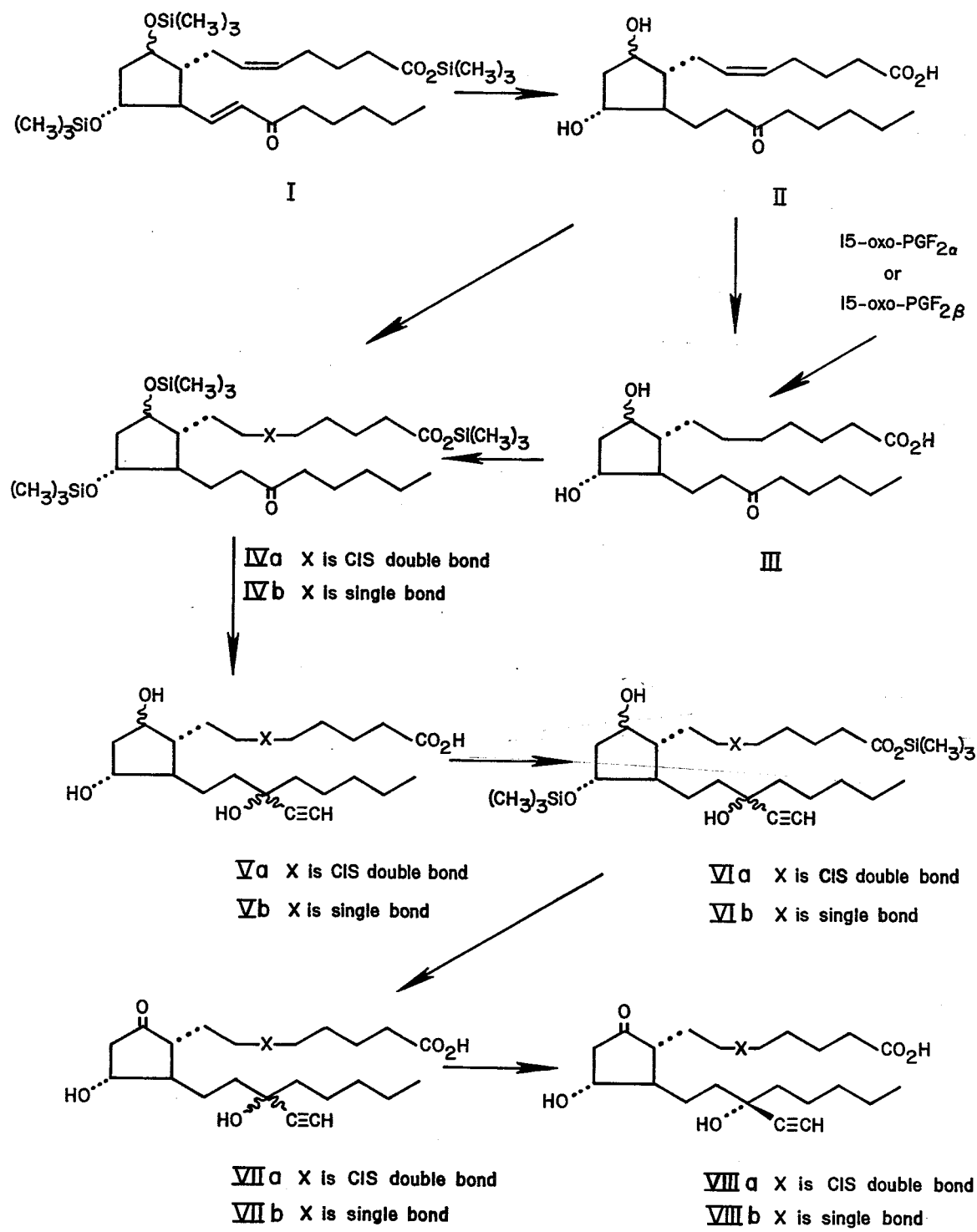

In describing the synthesis of the compositions of the invention, reference will be made to FIG. I, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilzed when representing the bonds of said substituents. Thus, with reference to the plane of paper, when a dashed line (----) is used, the substituent will be understood to be in the α (down) configuration; and when a heavy line (◄) is used, the substituent will be understood to be in the β (up) configuration; and when a wavy line (∿) is used both α and β configurations are contemplated for the substituent. Thus, for example, when a new assymetric center is created by a below-described reaction, for example the addition of a Grignard reagent to a ketone, since both possible configurations for the new substituents will be produced they will be denoted by wavy lines (∿). Both of said isomers, unless otherwise noted, are considered to be full equivalents for the purposes of this invention. The formulae in FIG. I are either free carboxylic acids or trimethylsilyl esters. It will be obvious to those skilled in the art that the trimethylsilyl esters may be converted to their respective free acids by, for example, hydrolysis with dilute acid and the free acids may readily be treated to produce conventional alkyl esters as for example, with diazomethane, or with an alkanol and the proper catalyst or the free acids may be converted to an alkali metal or basic amine salt. The esters, salts and free acids are considered to be full equivalents for the purposes of the invention. Finally, the use of specific embodiments in FIG. I to illustrate the invention is merely descriptive and is not intended to delimit the scope of the invention.

Referring now to FIG. I, the tris-trimethylsilylated derivatives of 15-oxo-PGF$_{2\alpha}$ and 15-oxo-PGF$_{2\beta}$ (I) are known compounds and may be prepared as described in for example U.S. Pat. No. 3,804,889. It will be obvious to those skilled in the art that since the final products prepared as described by FIG. I contain a 9-keto function, which function is produced by the oxidation of a 9-hydroxyl function, that the stereochemical configuration of the 9-hydroxyl function is of little or no consequence as the oxidation of either will produce the same ketone. Thus, for purposes of the instant description, 15-oxo-PGF$_{2\alpha}$, 15-oxo-PGF$_{2\beta}$ and the respective intermediates derived therefrom are to be considered substantial equivalents. The 13,14 double bond (using the prostanoic acid numbering system) of I is reduced utilizing for example, lithium in liquid ammonia and after removal of the trimethylsilyl protecting groups II is produced. The 5,6 double bond of II may next be reduced as for example, with H$_2$/Pd/C to produce III which after trimethylsilylation (see for example, U.S. Pat. No. 3,804,889) produces IVb. III may also be obtained directly from 15-oxo-PGF$_{2\alpha}$ or PGF$_{2\beta}$ by reduction with H$_2$/Pd/C. Alternatively, II may be trimethylsilylated producing IVa. The keto function of IV is next ethynylated with an ethynyl metallic reagent, for example, ethylnyl magnesium bromide (conveniently prepared in situ). The acidic "work-up" of this reaction removes the trimethylsilyl protecting groups and V is isolated. The introduction of the C-15 ethynyl group is non-stereospecific, thus compounds containing this substituent are isomeric mixtures at C-15 and the substituent bonds at C-15 are thus represented by wavy (∿) lines. As described below, these isomers may be separated by, for example, chromatographic means. Compound V is next selectively trimethylsilylated with trimethylsilyldiethylamine in, for example, acetone solution at about −+° C. producing the bis-trimethylsilyl derivative VI. The 9-hydroxyl function (in either the α or β stereochemical configuration) is next oxidized with, for example, Collins reagent, producing VII, which may, if desired, be separated into its two component C-15 isomers by, for example, chromatographic means. In this manner, compound VIII is isolated.

When used herein and in the appended claims, the term "alkali metal" includes, for example, sodium, potassium, lithium, and the like. A "pharmacologically acceptable cation derived from ammonia or a basic amine" contemplates the positively charged ammonium ion and analogous ions derived from organic nitrogenous bases strong enough to form such cations. Bases useful for the purpose of forming pharmacologically acceptable non-toxic addition salts of such compounds containing free carboxyl groups form a class whose limits are readily understood by those skilled in the art. Merely for illustration, they can be said to comprise, in cationic form, those of the formula:

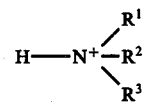

wherein R$^1$, R$^2$, and R$^3$, independently, are hydrogen, alkyl of from 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms or, when taken together with the nitrogen atom to which they are attached, any two of R$^1$, R$^2$, and R$^3$ form part of a 5 to 6-membered heterocyclic ring containing carbon, hydrogen, oxygen, nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and tri-methylammonium, mono-, di-, and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolodinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris(hydroxymethyl)methylammonium, phenylmonoethanolammonium, and the like.

The following examples further illustrate the best mode contemplated by the inventor for the practice of the invention.

EXAMPLE 1

13,14-Dihydro-15-Oxo-PGF$_{2\beta}$-Trimethylsilyl Ether, Trimethyl Silyl Ester (IVa)

Collect liquid ammonia (100 ml.) in a two necked 500 ml. round bottom flask equipped with dry ice condenser. Add a mixture of toluene (30 ml.) and dry tetrahydrofuran (30 ml.) rapidly dropwise. Add lithium ribbon (400 mg.) in small portions to the ammonia/- toluene/THF mixture. Then dissolve in a mixture of toluene (20 ml.) and THF (20 ml.) the tris-trimethyl silyl derivative of 15-oxo-PGF$_{2\beta}$ prepared previously from 15-oxo-PGF$_{2\beta}$ (3.6 g.). Stir the reaction mixture for six minutes after complete addition of the silyl derivative. Add ethylene dibromide dropwise until the blue color is discharged. Then cautiously add a mixture of glacial acetic acid (3 ml.) in methanol (12 ml.), with vigorous stirring. Evaporate the ammonia, add water (100 ml.), acidify with acetic acid and evaporate the organic solvents. Extract the residue with ethyl acetate. Wash the extract with brine, dry over magnesium sulfate and evaporate, to obtain an oil, 13,14-dihydro-15-oxo-PGF$_{2\beta}$ trimethylsilyl ether, trimethylsilyl ester.

EXAMPLE 2

15-Oxo-Tetrahydro-PGF$_{2\alpha}$-Trimethylsilyl Ether Trimethyl Silyl Ester (IVb)

Pre-hydrogenate 10% palladium on charcoal (1.0 g.) in ethyl acetate (200 ml.), add a solution of 15-oxo-PGF$_{2\alpha}$ (3.7 g.) in ethyl acetate (100 ml.) and hydrogenate. Filter the catalyst and evaporate the filtrate to obtain 3.5 g. of III. Prepare the tris-trimethyl silyl derivative using the method described in U.S. Pat. No. 3,804,889.

EXAMPLE 3

13,14-Dihydro-15-Oxo-PGF$_{2\beta}$ (II)

Dissolve the trimethyl silyl derivative of 13,14-dihydro-15-oxo-PGF$_{2\beta}$ in a mixture of ethanol (35 ml.) and water (25 ml.) containing a few drops of acetic acid. Stir at room temperature for 60 minutes. Evaporate the ethanol. Add brine to the residue and extract with ethyl acetate. Wash the extract with brine, dry over magnesium sulfate and evaporate to obtain a light brown oil, yield 3.0 g.

Chromatograph the mixture over 300 g. of Mallinckrodt CC4 silica gel and elute successively with 1.5 liters of 50%, 2 liters of 60%, 1 liter of 70%, 1 liter of 80% and 1 liter of 90% ethyl acetate in hexane, collecting the corresponding eluates in 225–250 ml. fractions. Combine eluate fractions 22–27 to obtain 13,14-dihydro-15-oxo-PGF$_{2\beta}$. Mass spectral peaks at 552 (M-90), 537, 481, 462, 443, 353, 263 (fully silylated derivative).

EXAMPLE 4

13,14-Dihydro-15-Ethynyl PGF$_{2\beta}$ (Va)

Equip a flask with a magnetic stirrer, condenser and a gas inlet tube, add dry tetrahydrofuran (400 ml.) and saturate with purified acetylene gas. Add a solution of 3M etheral methyl magnesium bromide (60 ml.) in dry tetrahydrofuran (120 ml.) dropwise and stir for 40 minutes. Add a solution of the tris-(trimethylsilyl)-derivative of 13,14-dihydro-15-oxo-PGF$_{2\beta}$ (3.7 g. crude) in dry tetrahydrofuran (200 ml.) rapidly dropwise. Stir the resulting solution at room temperature for 4 hours. Cool in ice and add saturated ammonium chloride. Separate the layers, acidify the aqueous layer with acetic acid, and extract with ethyl acetate. Combine the organic phases, wash with brine, dry over magnesium sulfate and evaporate to obtain a crude oil. Treat the oil with a mixture of ethanol and water (60:30 v/v) containing a few drops of acetic acid. Stir the mixture at room temperature for 3 hours. Evaporate the ethanol. Add brine to the residue and extract with ethyl acetate. Wash the extract with brine, dry over magnesium sulfate and evaporate to obtain a crude residue, 3.2 grams.

Chromatograph the crude product on Mallinckrodt silicar CC4 silica gel (300 g.) and elute successively with 1.8 liters 70%, 1 liter 80%, 3 liters of 90% ethyl acetate in hexane, collecting the corresponding eluates in 200 ml. fractions. Combine fractions 15–27 to obtain 1.093 g. of 13,14-dihydro-15-ethynyl-PGF$_{2\beta}$. λmax film 3.1, 3.5, 5.8, 6.2, 6.8, 8.05, 9.2, 9.6, 10.8.

NMR Analysis: δ 0.9 (20-CH$_3$), 2.4 (C≡CH), 4.1 (m, 2p, 9 & 11-H), 4.6 (m, OH), 5.5 (m, 2p, olefinic). Gc-ms molecular weight of fully silylated derivative 668.

EXAMPLE 5

13,14-Dihydro-15-Ethynyl-PGF$_{2\beta}$-Trimethyl Silyl Ester-11-Trimethyl Silyl Ether (VIa)

Dissolve 13,14-dihydro-15(RS)-15-ethynyl PGF$_{2\beta}$ (900 mg.) in acetone (25 ml.) and cool to −30°. Add trimethylsilyldiethylamine (10 ml.) and stir under nitrogen for 3 hours. Add methanol (10 ml.), and warm to room temperature. Evaporate the solvent and dry in vacuo to obtain 13,14-dihydro-15-ethynyl PGF$_{2\beta}$-trimethyl silyl ester, 11-trimethyl silyl ether.

EXAMPLE 6

15-Ethynyltetrahydro-PGF$_{2\alpha}$ (Vb)

Follow the procedure of Example 4 to obtain from the tris-trimethylsilyl derivative of 15-oxo-tetrahydro-PGF$_{2\alpha}$ the title product.

Mass spectral analysis calculated for tetratrimethylsilyl derivative M$^+$ at m/e 670. Found M$^+$ at 670.

EXAMPLE 7

15-Ethynyl-Tetahydro-PGF$_{2\alpha}$ Trimethyl Silyl Ester-11-Trimethyl Silyl Ether (VIb)

Follow the procedures in Example 5 to obtain from 15-ethynyl-tetrahydro-PGF$_{2\alpha}$, the title product.

EXAMPLE 8

13,14-Dihydro-15-Ethynyl-PGE$_2$ (VIIa)

Prepare Collins reagent by adding chromium trioxide (1.0 g.) to a well stirred solution of pyridine (1.6 ml.) in methylene chloride (50 ml.) and stir for 30 minutes. Add a solution of 13,14-dihydro-15-ethynyl-PGF$_{2\beta}$ trimethylsilyl ester-11-trimethyl silyl ether in methylene chloride rapidly dropwise and stir at room temperature for 60 minutes. Filter the mixture. Add sufficient ethyl acetate and ether to render the organic phase lighter than water. Wash the organic phase with brine, dry over magnesium sulfate and evaporate to obtain a brown oil.

Treat this oil with a mixture of methanol and water (30:15 v/v) and stir the solution for 1 hour. Partition this solution between ether and 2 molar sodium bisulfate solution. Extract the aqueous phase with ethyl acetate. Wash the combined organic phase with brine, dry over magnesium sulfate and evaporate to obtain a brown oil. Crude yield 395 mg.

Chromatograph the crude product on Mallinckrodt Silicar CC4 (30 g.). Elute successively with 380 ml. 50%, 60 ml. 60% and 100 ml. 90% ethyl acetate in hexane, collecting the corresponding eluates in 20 ml. fractions. Combine fractions 11–16 to obtain 13,14-dihydro-15-ethynyl PGE$_2$ (70 mg.) λmax film 3.05, 3.4, 5.75, 6.85, 7.2, 8.1, 8.6, 9.3, 13.2.

NMR Analysis: δ 0.9 (20-CH$_3$), 2.5 (C CH), 4.1 (11-H), 5.5 (m,olefinic + OH) ppm. Gc-ms molecular weight (trisilyl derivative) 594.

EXAMPLE 9

15-Ethynyl-Tetrahydro-PGE$_2$ (VIIb)

Follow the procedures in Example 8 to obtain from 15-ethynyl-tetrahydro PGF$_{2\alpha}$ the title product.

I.R. Analysis: λmax film 3.05, 3.35, 5.7, 6.8, 7.2, 8.0, 8.6, 9.55, 10.65, 11.8.

NMR Analysis: Signals at δ=0.93 (20-CH$_3$), 2.53 (C C-H), 4.1 (11-H), 5.25 (OH), ppm.

Mass Spectral Analysis: Calc. for tetratrimethylsilyl derivative M$^+$ at m/e 668. Found M$^+$ at 668.

Chromatograph 500 mg. of the above prepared C-15 isomeric mixture on Mallinckrodt silicar CC4 (500 mg.). Elute successively with 140 ml. 40% ethyl acetate in hexane collecting three fractions. Continue by eluting with 160 ml. 40%, 280 ml. 50%, 100 ml. 55% and 80 ml. 60% ethyl acetate in hexane, collecting the corresponding eluates in 20 ml. fractions. Combine fractions 29–31 to obtain 15β-ethynyl-tetrahydro-PGE$_2$ (VIII).

Mass Spectral Analysis: Calc. for tetratrimethyl silyl derivative M$^+$ at m/e 668. Found M$^+$ at m/e 668.

EXAMPLE 10

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the does to produce bronchodilation is from about 0.15 micrograms to about 25 micrograms, and preferably from about 0.15 to about 15 micrograms. The bronchodilation produced upon aerosol inhalation can be observed by the method of Rosenthale et al., *J. Pharmacol. Exp. Ther.*, 178, 541 (1971). Using this procedure the following results were obtained:

| Compound | Dose (μg) | Percent Inhibition of the Bronchoconstricting effects of a standard dose* of acetylcholine |
|---|---|---|
| 13,14-dihydro-15-ethynyl-PGE$_2$ | .015 | 94 |

-continued

| Compound | Dose (μg) | Percent Inhibition of the Bronchoconstricting effects of a standard dose* of acetylcholine |
|---|---|---|
|  | .15 | 96 |
|  | 1.5 | 100 |
|  | 15 | 91 |
| 13,14-dihydro-15-ethynyl-PGF$_{2\beta}$ | 1.5 | 44 |
|  | 15 | 63 |
| tetrahydro-15-ethynyl-PGE$_2$ | .0015 | 51 |
|  | .015 | 86 |
|  | .15 | 99 |
|  | 1.5 | 100 |
| tetrahydro-15β-ethynyl-PGE$_2$ | .0015 | 58 |
|  | .015 | 95 |
|  | .15 | 98 |

*The dose (i.v.) of acetylcholine which produces a ca. 30% bronchoconstriction.

The subject matter which the Applicant regards as his invention is particularly pointed out and distinctly claimed as follows:

1. A chemical compound of the structure:

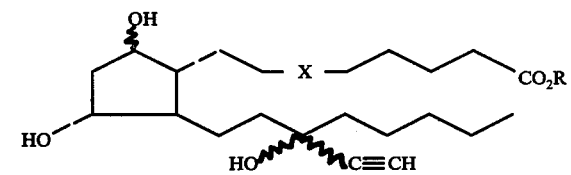

wherein X is a cis double bond, and R is hydrogen, alkyl of from 1 to 6 carbon atoms, an alkali metal cation, or a pharmacologically acceptable cation derived from ammonia or a basic amine.

2. The chemical compound of claim 1 which is:

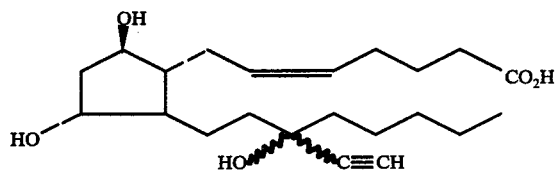

3. A chemical compound of the structure:

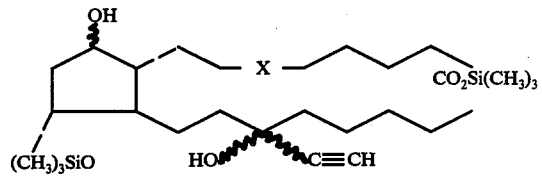

4. The chemical compound of claim 3 wherein the 9-OH substituent is in the β stereochemical configuration.

* * * * *